United States Patent [19]

Chen et al.

[11] Patent Number: 5,401,365
[45] Date of Patent: Mar. 28, 1995

[54] HIGH PURITY BENZENE PRODUCTION USING EXTRACTIVE DISTILLATION

[75] Inventors: George T. Chen, San Rafael; Brenda M. Balaban, Torrance, both of Calif.; Gerd Emmrich; Bernhard Firnhaber, both of Essen, Germany

[73] Assignee: Chevron Research & Technology, San Francisco, Calif.

[21] Appl. No.: 141,605

[22] Filed: Oct. 27, 1993

Related U.S. Application Data

[63] Continuation-in-part of Ser. No. 967,600, Oct. 28, 1992, abandoned.

[51] Int. Cl.⁶ .............................................. C07C 7/08
[52] U.S. Cl. ......................................... 203/32; 208/89; 203/58
[58] Field of Search ................... 203/32, 58; 208/89

[56] References Cited

U.S. PATENT DOCUMENTS

| | | | |
|---|---|---|---|
| 3,434,936 | 3/1969 | Luther et al. | 203/32 |
| 4,191,615 | 3/1980 | Schulze et al. | 203/3 |
| 4,456,527 | 6/1984 | buss | 208/89 |
| 4,997,547 | 3/1991 | Emmrich et al. | 208/313 |
| 5,031,754 | 7/1991 | Emmrich et al. | 203/58 |
| 5,139,651 | 8/1992 | Forte | 208/334 |
| 5,180,474 | 1/1993 | Skatulla et al. | 203/84 |

*Primary Examiner*—James H. Reamer
*Attorney, Agent, or Firm*—Burns, Doane, Swecker & Mathis

[57] ABSTRACT

A process is provided for separating benzene from non-aromatics in a highly aromatic stream containing olefins in a concentration range of from about 0.05 to about 5.0, which process comprises predistilling said highly aromatic stream to produce a distilled fraction having a concentration of $C_8$ and heavier compounds of less than about 0.1 wt percent; and extracting said distilled fraction with a solvent comprising substituted morpholines in an extractive distillation zone to produce a highly-pure benzene stream.

7 Claims, 1 Drawing Sheet

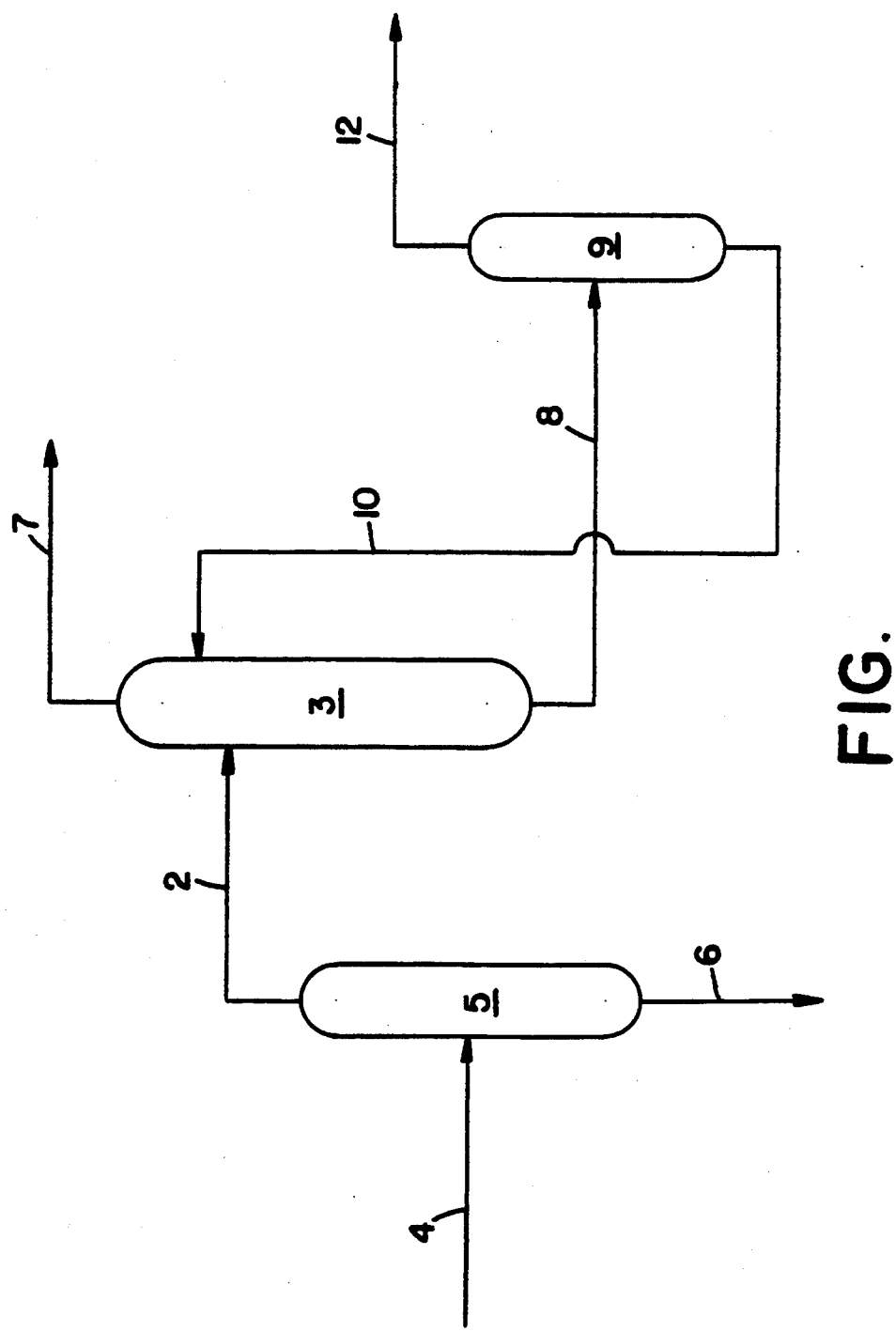

HIGH PURITY BENZENE PRODUCTION USING EXTRACTIVE DISTILLATION

CROSS-REFERENCE TO RELATED APPLICATIONS

This application is a continuation-in-part of U.S. Ser. No. 967,600, filed Oct. 18, 1992, now abandoned.

BACKGROUND OF THE INVENTION

The present invention relates to a process for recovering benzene from a highly aromatic reformate containing olefins.

Processes for the production of benzene from hydrocarbon feedstock are well-developed in the art. In particular, one recent advance in benzene-producing technology in a process comprises contacting a hydrocarbon feed of ultra-low sulfur level with a platinum containing zeolite catalysts resulting in a highly aromatic product stream. U.S. Pat. No. 4,456,527, issued Jun. 26, 1984 to Buss et al. assigned to the assignee of the present invention discloses such a process, and is incorporated by reference herein.

Extraction processes, such as the "sulfolane" and UDEX are frequently used to extract aromatics from conventional reformate. These processes are liquid/liquid extractions and are effective when feed aromatics concentrations are usually below 50%. However, at aromatics concentrations above about 50%, liquid/liquid extraction is no longer effective or economically viable. A highly aromatic reformate with high benzene concentration and about 0.05 wt % to about 5.0 wt. % olefins is not recoverable using liquid/liquid extraction.

The customary methods, today, of attaining higher purities, are liquid phase extraction and extractive distillation. The first method is preferred when more than one aromatic compound, such as benzene and/or toluene and/or xylenes, is to be commonly recovered from aromatic feedstocks which contain relatively large quantities (more than 30% wt.) of non-aromatics, as is the case with the gasoline fraction from reformers. It was generally thought that extractive distillation offers economical advantages when only one aromatic is to be removed from a corresponding cut, if its content of non-aromatics is relatively small (below 30% wt.). The latter is particularly the case with feedstocks like hydrorefined coke oven benzole and hydrogenated pyrolysis gasoline from steam-crackers. These feedstocks contain toluene and xylenes typically only in small fractions, and often only benzene is recovered. The cuts containing toluene and xylenes are frequently admixed with motor fuels in order to increase the octane number.

Under some conditions, extractive distillation has been demonstrated to be an attractive benzene recovery process for streams having an aromatics concentration greater than about 35%. Extractive distillation processes have been used in the production of pyrolysis gasoline, or "pygas". However, pygas production processes include selective hydrogenation of olefins prior to the extractive distillation step, as the feedstreams typically contain high levels of olefinic compounds, which are undesirable.

In a hydrocarbon reforming and recovery process it is desirable to eliminate this hydrogenation step for economic reasons.

U.S. Pat. No. 3,434,936 issued Mar. 25, 1969 to Luther et al. describes a method of separating aromatic compounds from hydrocarbon streams by extractive distillation with an N-substituted morpholane. U.S. Pat. No. 3,434,936 also describes the problem of polymerization of compounds in the sump of an extractive distillation unit, and the need to hydrogenate the unsaturated compounds in the extract from the extractive distillation unit.

An improved process for the production of a highly pure benzene stream from a highly aromatic stream containing olefins is much desired.

SUMMARY OF THE INVENTION

In accordance with our present invention, a process is provided for separating benzene from non-aromatics in a highly aromatic stream containing olefins in a concentration range of from about 0.05 to about 5.0, preferably 0.5 weight percent to about 3.0 weight percent, which process comprises: (a) predistilling said highly aromatic stream to produce a distilled fraction having a concentration of $C_8$ and heavier compounds of less than about 0.1 wt percent; and (b) extracting said distilled fraction with a solvent comprising substituted morpholines in an extractive distillation zone to produce a highly-pure benzene stream.

Among other factors, the present invention is based on our conception of the above process and on our finding that when a highly aromatic stream containing olefins is predistilled to remove high boilers, detrimental dimerization reactions do not appreciably occur in the extractive distillation zone. Therefore, hydrogenation prior to or following the extractive distillation step is not required to meet benzene product specifications. Surprisingly, we was also found that, in the process of our present invention, that the olefinic compounds which are known to be a major problem in the purification of highly aromatic feedstocks are carried overhead in the extractive distillation column, thus achieving a highly pure benzene product stream and eliminating the need for a clay post-treatment, hydrogenation, or the like.

BRIEF DESCRIPTION OF THE DRAWING

The FIGURE of the Drawing schematically depicts a process for separating benzene from non-aromatics in accordance with the present invention.

DETAILED DESCRIPTION OF THE INVENTION

By the term "highly aromatic" we mean having a concentration of aromatic compounds greater than about 35 weight percent, preferably greater than about 50 weight percent, most preferably greater than about 60 weight percent aromatics.

By the term "highly-pure benzene", we mean greater than about 99.5 weight percent benzene, preferably greater than about 99.9 weight percent; and containing less than about 0.10 weight percent, preferably less than about 0.05 weight percent, most preferably less than about 0.01 weight percent olefinic compounds. Alternatively, the term "highly-pure benzene" means a benzene fraction having a bromine index preferably less than about 10.

By the term "extractive distillation" we mean a distillation process which uses a solvent to accentuate and/or invert the relative volatility of the components which are desired to be separated.

The process of our invention separates benzene from non-aromatics in a highly aromatic stream comprising between about 0.05 weight percent and about 5.0 preferably between about 0.5 weight percent and about 3.0 weight percent olefins. The first step of said process is the predistilling of the highly aromatic stream to produce a distilled fraction having a concentration of $C_8$ and heavier compounds less than about 0.1 weight percent. Because toluene may be present, preferably the predistillation step is a multi-stage distillation.

Referring now to the FIGURE, a highly aromatic stream 4 is introduced to the predistillation zone 5 wherein a $C_7$ and heavier fraction is removed in the bottoms, and a predominantly benzene containing stream 2 which also comprises between about 0.05 weight percent and about 5.0 weight percent, preferably between 0.5 weight percent and about 3.0 weight percent olefins is taken off the overhead of the predistillation zone 5.

A second step in the process of our invention is the extraction of the distilled fraction from the predistillation step with a solvent comprising N-substituted morpholines in an extractive distillation zone 3.

The substituted morpholines can have a substituent containing from one to seven carbon atoms. Illustrative examples of suitable solvents include N-formyl-2,6-dimethylmorpholine, N-formylmorpholine, N-oxyethyl-morpholine, N-acetylmorpholine and N-phenylmorpholine, or mixtures thereof. The substituent may be straight or branched chained or of cyclic structure. In addition, the substituents may contain hetero atoms adjacent C-atoms. Particularly preferred for the present invention are N-substituted-morpholines, especially N-formylmorpholine.

Referring to the FIGURE, the extractive distillation is carried out in zone 3, wherein aromatics are separated from non-aromatics. By the addition of the solvent in extractive distillation zone 3, the vapor pressures are altered in such a way that paraffins and naphthenes are carried to the top and removed in the overhead from the extractive distillation column. The extractive distillation zone 3 can include a stabilizer column prior to the benzene extraction column for removal of any $C_5$ and lighter components, if present in quantities above about 2 wt. percent. It is preferred, however, that stream 4 would have been depleted of $C_5$ and lighter components before entering the predistillation zone 5.

Stream 7 is removed from the extractive distillation zone. Stream 7 contains the non-aromatics and, as we discovered, substantially all the olefins initially present in the feed to the extractive distillation unit.

Surprisingly, we found that the contaminating olefins, including olefins with carbon numbers higher than the aromatics, were carried overhead in the extractive distillation column in stream 7. The rich solvent stream 8, containing solvent and benzene, is removed from the bottom of the extractive distillation zone 3 to a stripper zone 9. It is preferred that the extractive distillation be carried out without reflux, that is, without the return of hydrocarbons which have been distilled off. The column thus operates with "internal" reflux alone, and adjusts substantially by condensation of solvent within the column.

In the stripper zone 9, the solvent is separated from the rich solvent stream, preferably by distillation under vacuum conditions to produce a highly pure benzene stream 12 containing less than about 0.1 weight percent, preferably less than about 0.05 weight percent olefins. Lean solvent is returned to the extractive distillation zone 3 via line 10 for reuse in the extraction of benzene.

Various pumps, heat exchangers, valves, controls and the like have been omitted from the FIGURE and description for clarity, but will be readily recognized by those skilled in the art as both typical and necessary in carrying out the process of our present invention.

In a preferred embodiment of our invention, the highly aromatic feedstream to the predistillation zone is the product of an aromatization process comprising contacting an ultra-low sulfur naphtha with a large-pore, preferably type-L, platinum-containing zeolite catalyst under hydrocarbon reforming conditions. Such a process is described in U.S. Pat. No. 4,456,527, issued Jun. 26, 1984 to Buss, et al., which is incorporated by reference herein.

EXAMPLE

A feed having the composition shown in Table 1 is obtained from a non-acidic Pt-L-zeolite reforming process. In this example, the feed to the reforming process was a $C_6$ naphtha heartcut. Besides 54.20 wt. % benzene and 8.14 wt % toluene the stream may contain paraffins and olefins in the $C_3$ to $C_9$ range as well as aromatics up to very high boiling, polycyclic aromatics.

TABLE 1

| Analysis of Feed from Reforming Unit | |
|---|---|
| Component | wt % |
| $C_5$ and lighter | 1.7839 |
| $C_6$ Paraffins | 33.0100 |
| $C_6$ Olefins | 0.5920 |
| $C_6$ Naphthenes | 1.9460 |
| Benzene | 54.2000 |
| $C_7$ Paraffins | 0.0024 |
| $C_7$ Olefins | 0.2701 |
| $C_7$ Naphthenes | 0.0002 |
| Toluene | 8.1430 |
| Xylenes | 0.0178 |
| Ethylbenzene | 0.0180 |
| Other heavy components | 0.0166 |
| Total | 100.0000 |

It was decided to predistill the feed in order to remove the high boilers.

Distillation, at atmospheric pressure, was carried on until all the benzene and sufficient toluene was collected overhead. The reflux ratio was set at 1 up to an overhead vapor temperature of 85° C. Then the reflux ratio was increased to about 4 and distillation continued until the condensed overhead had a toluene content low enough to meet the desired benzene specifications.

The condensed overhead was then sent to an extractive distillation column.

Extractive Distillation Test

The extractive distillation column, Extractive Distillation ("ED") was followed by a stripper column, Stripper.

The lower part of the ED column had 30 trays, one bubble cap per tray. Both columns had two bottom reboilers, one on top of the other. Heat input was normally controlled by a temperature in the upper part of the column. The result of the test run is determined by gas chromatographic analysis of the product streams.

Various tests were carried out with 200 l of feedstock of overhead from the predistillation step. The conditions for the ED column were: pressure at top between 1.0 and 3.0 bar, feed rate equal to 4.0 l/h, and solvent to feed weight ratio equal to about 2.0–3.5. Conditions for the Stripper were as follows: pressure at top 0.4–1.5 bar, reflux ratio equal to about 1.0–3.0.

The unit was operated with feedstock twice continuously for 120 hours.

Test Results

Tests were carried out 2 or 3 times a day during relatively constant operations. For these tests samples were drawn simultaneously of the feed, the extractive distillation column overhead product (raffinate), the stripper overhead product (extract), and the stripped solvent. Complete analyses were carried out and heat balances were calculated.

An excellent separation was obtained between aromatics and non-aromatics. Benzene loss with the raffinate was only 0.1–1.0%, while the benzene containing extract product contained only about 30 ppm olefins, had a bromine index of generally 5 to 10 and a N-formyl-morpholine content of only less than 1.0 ppm.

We were quite surprised the olefin content of the extract product was so extremely low, given the level of unsaturated compounds in the feed to the process. The benzene product from the stripper section exceeded commercial specifications, without the need for a post treating step, such as washing with acid or treatment with bleaching or Fullers earth; or subjecting the product to hydrogenation.

Various modifications to the process of our present invention are possible in light of the,teachings supported by the specification, figure, and process example. Such obvious alterations are intended to be within the scope of the claims appended hereto.

What is claimed is:

1. A process for separating benzene from non-aromatics in a highly aromatic stream containing between about 0.5 and about 5.0 weight percent olefins, comprising:
   (a) predistilling said highly aromatic stream to produce a distilled fraction having a concentration of $C_8$ and heavier compounds of less than about 0.05 weight percent;
   (b) extracting said distilled feedstream with a solvent comprising N-substituted morpholines in an extractive distillation zone, to produce a highly-pure benzene stream.

2. The process as recited in claim 1, wherein said highly aromatic stream contains at least 50 weight percent benzene.

3. The process as recited in claim 2, wherein the N-substituted morpholines contain at least 90 weight percent N-formyl-morpholine.

4. A process for producing a highly pure benzene, comprising:
   (a) contacting a hydrocarbon feedstream having a sulfur concentration of less than about 100 parts per billion with a non-acidic L-type zeolite catalyst comprising platinum under reforming conditions to produce a highly aromatic stream and hydrogen, said highly aromatic stream comprising benzene, non-aromatics and between about 0.5 and about 5.0 weight percent olefins,
   (b) distilling said highly aromatic stream to produce a distilled feedstream having a concentration of $C_8$ and heavier compounds of less than about 0.05 wt percent;
   (c) extracting said distilled feedstream with a solvent comprising N-substituted morpholines in an extractive distillation zone, and;
   (c) removing from said extractive distillation zone a highly-pure benzene stream.

5. The process as recited in claim 4 wherein the highly pure benzene stream contains greater than about 99.9 weight percent benzene.

6. The process as recited in claim 4 wherein the highly pure benzene stream contains less than about 0.1 weight percent olefins.

7. The process as recited in claim 5 wherein the highly pure benzene stream contains less than about 0.05 weight percent olefins.

* * * * *

UNITED STATES PATENT AND TRADEMARK OFFICE
CERTIFICATE OF CORRECTION

PATENT NO. : 5,401,365
DATED : March 28, 1995
INVENTOR(S) : George T. CHEN, et al.

It is certified that error appears in the above-indentified patent and that said Letters Patent is hereby corrected as shown below:

On the title page,
  Change line [73] from Chevron Research & Technology, San Francisco, Calif.

to

--Chevron Chemical Co., San Francisco, California
    AND
    Krupp Koppers, GmbH, Essen, Germany--.

Signed and Sealed this

Twelfth Day of November, 1996

Attest:

BRUCE LEHMAN

*Attesting Officer*      *Commissioner of Patents and Trademarks*